United States Patent
Ho et al.

(10) Patent No.: US 9,199,048 B2
(45) Date of Patent: Dec. 1, 2015

(54) AUTOMATIC IDENTIFICATION OF A PATIENT INTERFACE DEVICE IN A PRESSURE SUPPORT SYSTEM

(75) Inventors: Peter Chi Fai Ho, Pittsburgh, PA (US); Zachary Dean Paul, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 633 days.

(21) Appl. No.: 13/512,980

(22) PCT Filed: Nov. 16, 2010

(86) PCT No.: PCT/IB2010/055203
§ 371 (c)(1), (2), (4) Date: May 31, 2012

(87) PCT Pub. No.: WO2011/077274
PCT Pub. Date: Jun. 30, 2011

(65) Prior Publication Data
US 2012/0247470 A1    Oct. 4, 2012

Related U.S. Application Data

(60) Provisional application No. 61/288,457, filed on Dec. 21, 2009.

(51) Int. Cl.
*A61M 16/06* (2006.01)
*A61M 16/00* (2006.01)

(52) U.S. Cl.
CPC ........ *A61M 16/0066* (2013.01); *A61M 16/0051* (2013.01); *A61M 16/0069* (2014.02); *A61M 16/06* (2013.01); *A61M 2016/0027* (2013.01); *A61M 2016/0039* (2013.01); *A61M 2205/13* (2013.01); *A61M 2205/14* (2013.01); *A61M 2205/52* (2013.01); *A61M 2205/60* (2013.01); *A61M 2205/6018* (2013.01); *A61M 2205/702* (2013.01)

(58) Field of Classification Search
CPC ............... A61M 2016/0027; A61M 2016/003; A61M 2016/0033; A61M 2016/0036; A61M 2016/0042; A61M 16/0051; A61M 16/08; A61M 16/0816
USPC ............................ 128/203.14, 22, 204.21–23
See application file for complete search history.

(56) References Cited

U.S. PATENT DOCUMENTS 5,632,269 A * 5/1997 Zdrojkowski ............ 128/204.23
6,425,395 B1 * 7/2002 Brewer et al. ............ 128/202.22
(Continued)

FOREIGN PATENT DOCUMENTS

WO    WO03000015 A2    1/2003
WO    WO2006092001 A1    9/2006
(Continued)

*Primary Examiner* — Jackie T Ho
*Assistant Examiner* — Joseph D Boecker
(74) *Attorney, Agent, or Firm* — Michael W. Haas

(57) ABSTRACT

A pressure support system includes a pressure generator, a pressure sensor, a flow sensor, and a controller cooperating with the pressure sensor and the flow sensor to control operation of the pressure generator. The controller is structured to automatically identify a patient interface device in use with the pressure support system by detecting a change of exhaust flow of up to a predetermined amount across a predetermined pressure gradient of a pressure range of the pressure support system.

16 Claims, 3 Drawing Sheets

(56) References Cited

U.S. PATENT DOCUMENTS

| | | | |
|---|---|---|---|
| 6,546,930 B1* | 4/2003 | Emerson et al. | 128/204.21 |
| 7,100,608 B2* | 9/2006 | Brewer et al. | 128/204.23 |
| 7,770,579 B2* | 8/2010 | O'Connor et al. | 128/204.21 |
| 7,913,689 B2* | 3/2011 | Henry et al. | 128/204.21 |
| 8,020,555 B2* | 9/2011 | Rapoport | 128/204.21 |
| 8,056,559 B2* | 11/2011 | O'Connor et al. | 128/204.21 |
| 8,267,084 B2* | 9/2012 | Kwok | 128/204.21 |
| 8,496,001 B2* | 7/2013 | Schermeier et al. | 128/202.22 |
| 8,616,202 B2* | 12/2013 | Tatkov et al. | 128/203.17 |
| 8,714,153 B2* | 5/2014 | Scarberry et al. | 128/204.23 |
| 8,789,528 B2* | 7/2014 | Carter et al. | 128/204.21 |
| 2007/0277824 A1 | 12/2007 | Aylsworth | |
| 2011/0120462 A1* | 5/2011 | Tatkov et al. | 128/203.14 |

FOREIGN PATENT DOCUMENTS

| | | |
|---|---|---|
| WO | WO2008091164 A1 | 7/2008 |
| WO | WO2009136333 A1 | 11/2009 |

\* cited by examiner

AUTOMATIC IDENTIFICATION OF A PATIENT INTERFACE DEVICE IN A PRESSURE SUPPORT SYSTEM

CROSS-REFERENCE TO RELATED APPLICATIONS

This patent application claims the priority benefit under 35 U.S.C. §371 of international patent application no. PCT/IB2010/055203, filed Nov. 16, 2010, which claims the priority benefit under 35 U.S.C. §119(e) of U.S. Provisional Application No. 61/288,457 filed on Dec. 21, 2009, the contents of which are herein incorporated by reference.

BACKGROUND OF THE INVENTION

1. Field of the Disclosure

The present invention pertains to apparatus employed in the delivery of a flow of breathing gas to the airway of a patient, and, more particularly, to pressure support system that automatically identifies a patient interface device that is coupled to a pressure generating system.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a respiratory patient interface device, including a mask component, on the face of a patient. The mask component may be, without limitation, a nasal mask that covers the patient's nose, a nasal cushion having nasal prongs that are received within the patient's nares, a nasal/oral mask that covers the nose and mouth, or full face mask that covers the patient's face. The patient interface device interfaces the ventilator or pressure support device with the airway of the patient so that a flow of breathing gas can be delivered from the pressure/flow generating device to the airway of the patient.

It is common for users of pressure support devices to have several different patient interface devices (e.g., different masks and different patient interface components), tubing options, exhaust assemblies, or other component options (such as bacteria filters) that they use for reasons such as comfort. It is important for the pressure support device to know which type of patient interface device or other component is being used so that it will know certain information about the components, such as, without limitation, mask resistance, mask compliance, mask leak rates. Based on this information, the pressure support device can adjust the operating parameters of the unit. In addition, certain comfort features or device functions can be enabled on the basis of a particular mask or peripheral being attached.

Non-invasive ventilation and pressure support therapies are often based on a software driven mode that determines a breath-per-breath characteristic, such as, for example, the delivered or output pressure. The patient interface device being used often provides a specific exhaust flow pattern or characteristic, which is part of the computation of the output pressure. An effective and quick detection of the patient interface device in use and, hence, the exhaust flow characteristic can improve the accuracy of the output pressure computation.

A patient interface device typically includes three different types of leaks: total, intentional, and unintentional. The total leak is the sum of the intentional leak and the unintentional leak. The intentional leak is designed into the patient interface device (e.g., without limitation the exhaust assembly provided in the mask and/or patient circuit), in order that the patient does not re-breathe their own $CO_2$. The unintentional leak is, for example, an annoying leak that hits the patient in the eyes. Hence, it is desired to minimize the unintentional leak. However, it is believed that unlike the total leak, the unintentional leak cannot be measured.

It is known to determine and report the unintentional leak by measuring the total leak while the patient is using the patient interface device (e.g., which total leak can be measured at the beginning of the night) and then subtracting the intentional leak.

It is known to detect the patient interface device in use with a ventilator by sensing the exhaust flow rate and looking for a specific flow pattern that is proportional to the pressure. See, for example, curve 1 in FIG. 1. In other words, such a ventilator looks for a specific flow point at a given pressure point. It is also known to employ different styles of patient interface devices that span a relatively large range of intentional leak rates. This involves several curves (not shown) like curve 1 of FIG. 1, which are parallel to one another. For reporting the type of patient interface device in use, there is a gradually increasing pressure test to determine if the device in use corresponds to a parallel curve (not shown) toward a bottom range, toward a middle range or toward an upper range of intentional leak. Based on this determination (upper, middle or bottom), the ventilator uses the corresponding intentional leak value (not shown) to subtract from the measured total leak in the calculation of the unintentional leak. However, it is believed that there is no change in therapy delivered by the ventilator, only in what it reports.

SUMMARY OF THE INVENTION

As one aspect of the invention, a pressure support system comprises a pressure generator, a pressure sensor, a flow sensor, and a controller cooperating with the pressure sensor and the flow sensor to control operation of the pressure generator. The controller is structured to automatically identify a patient interface device in use with the pressure support system by detecting a change of exhaust flow of up to a predetermined amount across a predetermined pressure gradient of a pressure range of the pressure support system.

As another aspect of the invention, a method of automatically identifying a patient interface device in use with a pressure support system comprises: inputting a plurality of flow rates from a flow sensor; inputting a plurality of corresponding pressure points from a pressure sensor; employing the flow rates and the pressure points to detect a change of exhaust flow of up to a predetermined amount across a predetermined pressure gradient of a pressure range of the pressure support system; and comparing one of the flow rates and one of the corresponding pressure points to a plurality of predetermined flow rates and a number of predetermined pressure points to determine a type of mask as the patient interface device in use.

The disclosed method and apparatus can detect the patient interface device in use automatically during a pressure support ventilating therapy based, for example, on either nil or minimal intentional exhaust flow variation across a particular pressure gradient. For example and without limitation, this can identify the patient interface device in use by detecting a nil or minimal exhaust flow variation or change (e.g., without limitation, about 1% to about 25% change) across a significant pressure gradient (e.g., without limitation, 5%, such as 1 cmH$_2$O for a common CPAP machine with a 20 cmH$_2$O pressure output range; 25% of the pressure range of a pressure support system; about 50%, such as greater than 10 cmH$_2$O for a common CPAP machine with a 20 cmH$_2$O pressure output range; about 100%).

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
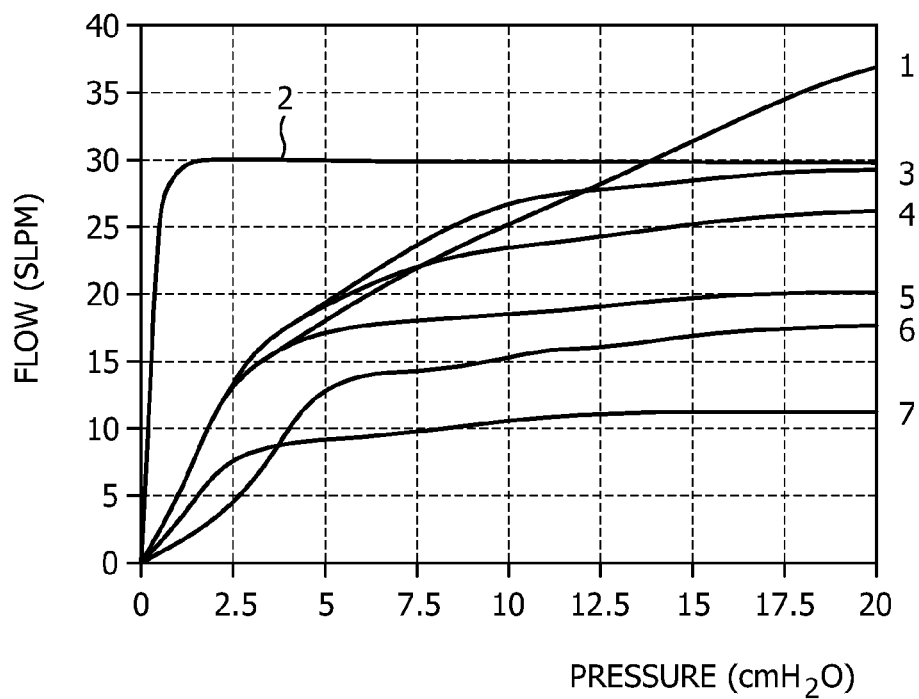
FIG. 1 is a plot of a plurality of different exhaust flow curves of flow versus pressure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the term "patient" means a human being or other members of the animal kingdom. As employed herein, the term "patient interface device" means a respiratory interface device, or a mask. As employed herein, the term "mask" means a patient interface or a patient interface mask providing or delivering air or gas flow to a patient, such as for example and without limitation, a face mask, a nasal mask, an oral mask, a nasal/oral mask, a nasal pillow, a total face mark, any other device or apparatus that provides or delivers a suitable air or gas flow communicating function to a patient; or a mask employed in treating sleep disorders of a patient.

As employed herein, the term "CPAP" means continuous positive airway pressure, which is a particular type of positive airway pressure ventilation (breathing) therapy. As employed herein, the term "COPD" means Chronic Obstructive Pulmonary Disease—a lung disease (e.g., without limitation, chronic bronchitis; emphysema).

Figure 2:
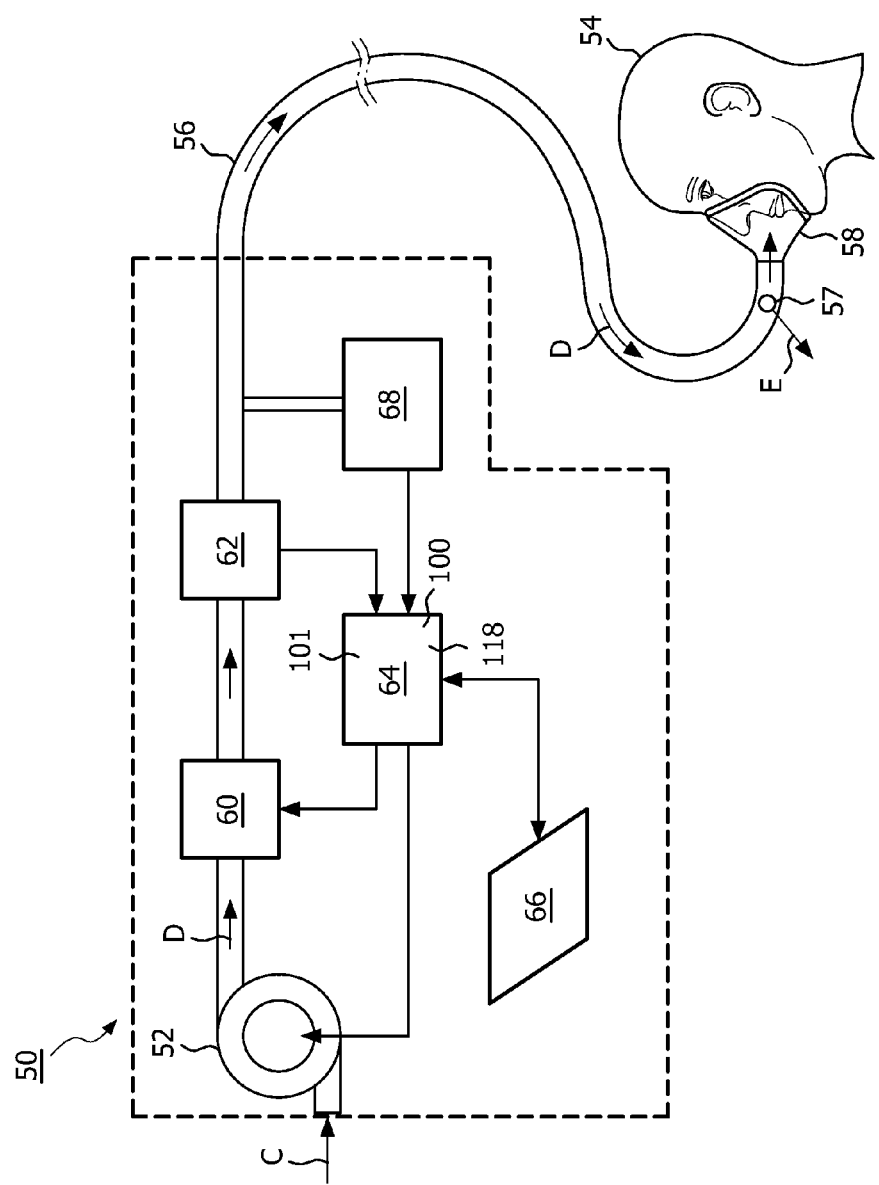
FIG. 2 is a block diagram in schematic form of a pressure support system in accordance with embodiments of the invention.

Referring to FIG. 2, pressure support system 50 includes gas flow generator 52, such as a blower used in a conventional continuous positive airway pressure (CPAP) or bi-level pressure support system, which receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway (not shown) of patient 54 at relatively higher and lower pressures, i.e., generally equal to or above ambient atmospheric pressure. Gas flow generator 52 is capable of providing a flow of breathing gas ranging in pressure from, for example and without limitation, about 3 cmH$_2$O to about 30 cmH$_2$O. The pressurized flow of breathing gas, generally indicated by arrow D from gas flow generator 52, is delivered via delivery conduit 56 to patient interface device 58, which is typically worn by or otherwise attached to patient 54 to communicate the flow of breathing gas to the airway of patient 54. Delivery conduit 56 and patient interface device 58 are typically collectively referred to as a patient circuit.

Pressure support system 50 is what is known as a single-limb system, meaning that patient circuit includes only delivery conduit 56 connecting patient 54 to pressure support system 50. As such, exhaust vent 57 is provided in delivery conduit 56 for venting exhaled gasses from the system as indicated by arrow E. Exhaust vent 57 can be provided at other locations in addition to or instead of in delivery conduit 56, such as in patient interface device 58. Exhaust vent 57 can have a wide variety of configurations depending on the desired manner in which gas is to be vented from pressure support system 50.

Pressure support system 50 can be a two-limb system, having a delivery conduit and an exhaust conduit connected to patient 54. In a two-limb system (also referred to as a dual-limb system), the exhaust conduit carries exhaust gas from patient 54 and includes an exhaust valve at the end distal from patient 54. The exhaust valve is typically actively controlled to maintain a desired level or pressure in the system, which is commonly known as positive end expiratory pressure (PEEP).

In an exemplary embodiment, pressure support system 50 includes a pressure controller in the form of valve 60 provided in delivery conduit 56. Valve 60 controls the pressure of the flow of breathing gas from flow generator 52 delivered to patient 54. Flow generator 52 and valve 60 are collectively referred to as a pressure generator because they act in concert to control the pressure and/or flow of gas delivered to patient 54. However, other techniques for controlling the pressure of the gas delivered to patient 54, such as varying the blower speed of flow generator 52, either alone or in combination with a pressure control valve, can be employed. Thus, valve 60 is optional depending on the technique used to control the pressure of the flow of breathing gas delivered to patient 54. If valve 60 is eliminated, the pressure generator corresponds to flow generator 52 alone, and the pressure of gas in patient circuit is controlled, for example, by controlling the motor speed of flow generator 52.

Pressure support system 50 further includes flow sensor 62 that measures the flow of the breathing gas within delivery conduit 56. Flow sensor 62 is interposed in line with delivery conduit 56, most preferably downstream of valve 60. Flow sensor 62 generates a flow signal that is provided to controller 64 and is used by controller 64 to determine the flow of gas at patient 54. Of course, other techniques for measuring the respiratory flow of patient 54 can be employed, such as measuring the flow directly at patient 54 or at other locations along delivery conduit 56 and communicating the measured flow by direct electrical connection between a flow sensor (not shown) and controller 64, measuring patient flow based on the operation of flow generator 52, and measuring patient flow using a flow sensor (not shown) upstream of valve 60.

Pressure support system 50 also includes pressure sensor 68 operatively coupled to controller 64 that detects the pressure of the gas at patient 54. Pressure sensor 68 is in fluid communication with patient interface device 58 via delivery conduit 56. The pressure at patient 54 is estimated based on the known pressure drop that occurs in delivery conduit 56. Alternatively, the patient pressure can be measured directly at patient interface device 58 using a pressure sensor (not shown) incorporated therein and communicating the measured pressure by direct electrical connection (not shown) between such pressure sensor (not shown) and controller 64.

Controller 64 may be, for example, a microprocessor, a microcontroller or some other suitable processor or processing device, that includes or is operatively coupled to a memory (not shown) that provides a storage medium for data and software executable by controller 64 for controlling the operation of pressure support system 50.

A user interface, such as input/output device 66, is provided for setting various parameters used by pressure support system 50, as well as for displaying and outputting information and data to a user, such as a clinician or caregiver or patient 54.

Pressure support system 50 can essentially function as a CPAP pressure support system, and, therefore, can include all of the capabilities necessary in such systems in order to provide appropriate CPAP pressure levels to patient 54. This includes receiving the necessary parameters, via input commands, signals, instructions or other information, for providing appropriate CPAP pressure, such as maximum and minimum CPAP pressure settings. Other pressure support methodologies, include but are not limited to, BiPAP AutoSV, AVAPS, Auto CPAP, and BiPAP Auto.

In the single-limb system, controller 64 estimates the leakage of gas from pressure support system 50 using any conventional technique and incorporates this leak estimation into the determination of the actual patient flow. This leak estimation is required in a single-limb system, because a single-limb system includes a known leak through exhaust vent 57 as well as other unknown leaks, such as leaks at the patient contact site of the patient interface device 58 and at various conduit couplings on patient circuit. In a two-limb system, leak estimation may not be required, because a flow sensor is typically provided at the exhaust vent to measure, directly, the flow of exhaust gas. In such a system, the patient flow can be determined by subtracting the measured exhaust flow from the measured flow delivered to the patient. It can be appreciated that leak detection can be performed in a two-limb system to increase the accuracy of the patient flow determination.

Figure 3:
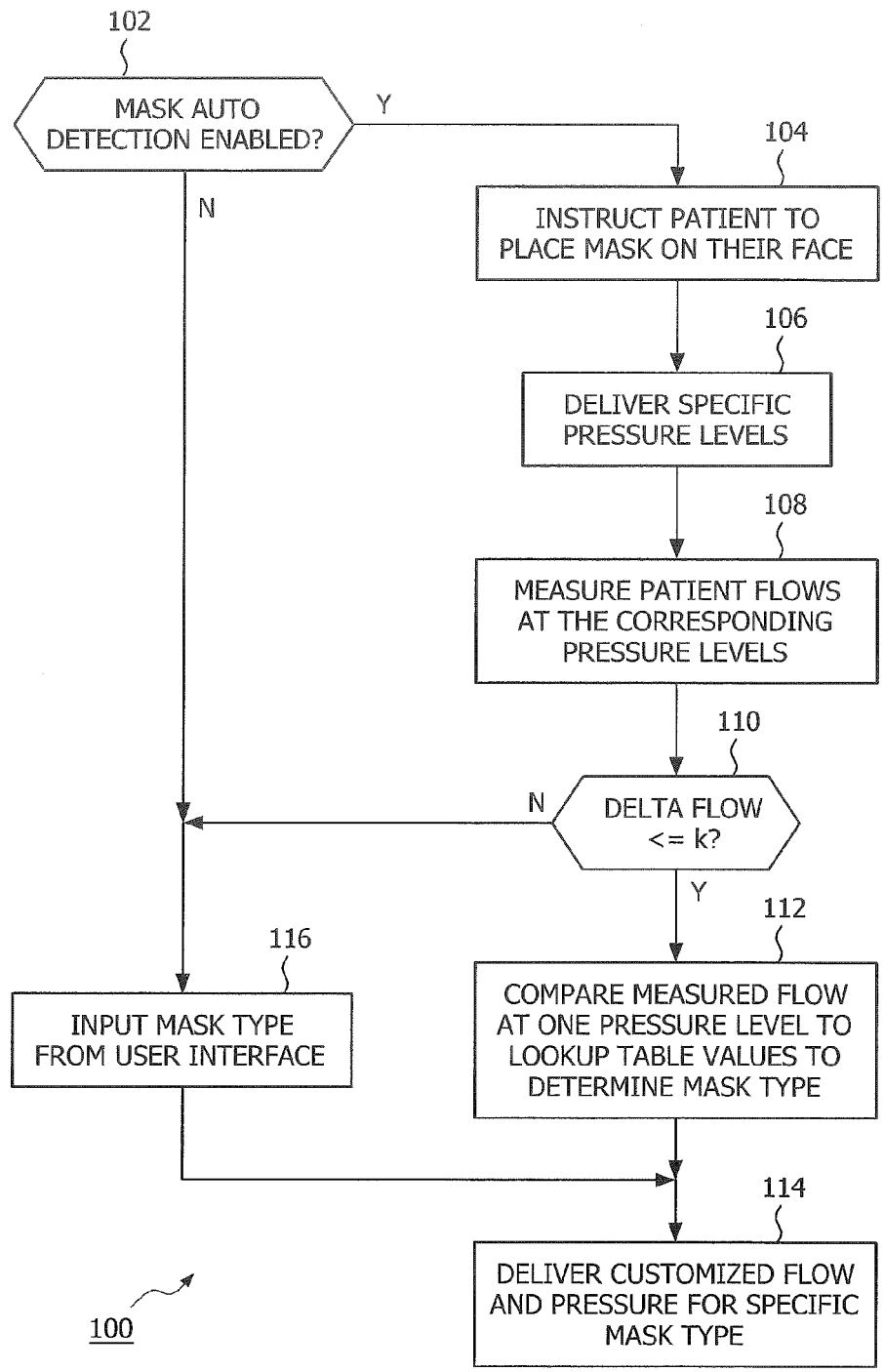
FIG. 3 is a flowchart of a routine executed by the controller of FIG. 2.

FIG. 3 shows a routine 100 executed by processor 101 of controller 64 of FIG. 2. First, at step 102, it is determined if the mask auto detection is enabled. This can be, for example and without limitation, a configuration parameter of controller 64. If so, then at step 104, patient 54 is instructed (e.g., through input/output device 66) to place, for example, patient interface device 58 (e.g., a particular type of mask unknown to controller 64) on their face. Providing a specific instruction to the patient is optional if the system detects that the user already has placed the patient interface in communication with his or her airway.

Next, at step 106, controller 64 functions to deliver specific pressure levels to patient 54 by controlling gas flow generator 52 and/or valve 60. Then, at 108, controller 64 measures, for example, two patient flows at two corresponding pressure levels from flow sensor 62 and pressure sensor 68, respectively.

Next, at step 110, it is determined if the delta flow (i.e., the difference between the two patient flows) of step 108 is less than a predetermined value, k. For example, routine 100 can identify a change of flow rate employing flow sensor 62, the change of flow rate being the difference between two different flow readings from flow sensor 62 taken at two different corresponding pressure points from pressure sensor 68. If the test passes at step 110, then at step 112, the measured flow at one pressure level is compared to, for example and without limitation, lookup table values to determine mask type as will be explained. Finally, at step 114, controller 64 causes delivery of customized flow and pressure to patient 54 based upon the mask type. For example, controller 64 can control the pressure generator to provide pressure and flow to the mask based upon the type of mask.

If the test failed at either step 102 or step 110, then patient 54 may be instructed (e.g., through input/output device 66) to manually input the mask type (e.g., as displayed on or with patient interface device 58) using input/output device 66.

After step 116, step 114 is executed as was discussed, above.

The example routine 100 provides a method of automatically identifying patient interface device 58 in use with pressure support system 50. This inputs a plurality of flow rates from flow sensor 62, inputs a plurality of corresponding pressure points from pressure sensor 68, employs the flow rates and the pressure points to detect a change of exhaust flow change of up to a predetermined amount across a predetermined pressure gradient of a pressure range of pressure support system 50, and compares one of the flow rates and one of the corresponding pressure points to a plurality of predetermined flow rates and a number of predetermined pressure points to determine a type of mask as the patient interface device 58 in use.

EXAMPLE 1

For example and without limitation, at step 110, if the detected exhaust flow change is greater than about 25% across the predetermined pressure gradient of the pressure range of pressure support system 50, then controller 64 requests manual input from input/output device 66 of the type of mask in use.

EXAMPLE 2

Although routine 100 is normally executed at startup, it will be appreciated that controller 64 can execute the same routine 100 or a similar routine (e.g., including steps 106, 108, 110 and 112) at other times to identify patient interface device 58, which is in use.

EXAMPLE 3

As can be seen, for example, with reference to FIGS. 1 and 3, if the test at step 110 passes, then at step 112, routine 100 can employ a flow rate from flow sensor 62 and a corresponding pressure point from pressure sensor 68, and compare that flow rate and corresponding pressure point to a plurality of predetermined flow rates and a number of predetermined pressure points (e.g., without limitation, in a lookup table 118 in memory (not shown) of controller 64 to determine the mask type). For example, and without limitation, if the example flow rate is 30 SLPM (standard liters per minute) and the example corresponding pressure point is 10 cmH$_2$O, then the mask type corresponds to curve 2 (e.g., without limitation, lookup table 118 can define six different mask types to curves 2, 3, 4, 5, 6, 7, respectively).

EXAMPLE 4

Step 114 of FIG. 3 controls the pressure generator to provide pressure and flow to patient interface device 58 based upon the type of mask.

EXAMPLE 5

Routine 100 and flow sensor 62 detect a constant or nearly constant flow with a flow variation tolerance (e.g., without limitation, as low as about 1 SLPM; as high as about 5 SLPM) depending on the given pressure gradient. After 110 and 112, routine 100 computes, at 114, the output flow and pressure based on a specific relatively constant flow curve corresponding to the specific patient interface device 58 in use employing PEV™ technology. See, for example, International Patent Application Pub. No. WO/2009/136333 and U.S. Provisional Patent Application No. 61/051,093, filed May 7, 2008. This can be further explained with reference to exhaust flow curves of FIG. 1.

Curve 1 is a conventional exhaust flow curve employed by a typical patient interface device without PEV™ technology. Curves 2 to 7 are various exhaust flow curves employed by a patient interface device, such as 58, with PEV™ technology. Each patient interface device with PEV™ technology can provide its own "constant" or nearly constant flow rate depending on the desired therapy. For example, curve 2 is an ideal flow curve for treating COPD patients with a flat 30 SLPM exhaust rate (detecting the exhaust flow change of about 0% and responsively determining a predetermined type of mask as patient interface device 58 in use), while curves 3-7 are flow curves for treating sleep apnea patients which prefer to have a non constant flow exhaust rate proportional to pressure in the low pressure range in order to preserve moisture. The constant pressure segment is onset from a specific pressure point. For example, curve 7 has the onset point at about 3 cmH$_2$O, while curve 5 has the onset point delayed to about 5 cmH$_2$O.

Step 110 of routine 100 (FIG. 3) looks for the lack of significant change in exhaust flow over one pressure gradient or multiple pressure gradients in order to determine the mask type.

During operation of pressure support system 50 (FIG. 2), patient exhalation is purged by a continuous leakage (or intentional leak) through a fixed opening (e.g., without limitation, exhaust vent 57; hole; array of holes; slot; slit; array of slits). The flow is not constant and varies with pressure due to the nature of the fixed opening. Pressure varies to compensate for the intentional leak to maintain pressure ventilating therapy. These compensations are computed by routine 100 based on known pressure-flow characteristics input for certain styles or groups of interfaces. For example, routine 100 tells gas flow generator 52 to increase RPM to deliver more flow and, thus, at a higher pressure than before in order to overcome the pressure drop caused by the leakage. Step 114 uses the specific mask type and corresponding stored pressure-flow data.

In FIG. 2, between gas flow generator 52 and patient 54 there is a flow resistance. Each component in the circuit from gas flow generator 52 to patient 54, including patient interface device 58, has its own resistance, which can be considered as being a leak instead of a resistance. Each component has a relatively very small unintentional leak and a relatively higher intentional leak in order to purge CO$_2$ (from exhalation). Each leak can now be understood as being a flow resistance. Each of the component flow resistances affects the pressure as a pressure drop. The therapy is to deliver pressure to patient 54. The various component pressure drops reduce the pressure that reaches patient 54. Hence, flow needs to be increased in order to make up the difference. Pressure is generated from flow by gas flow generator 52 and/or valve 60.

In the disclosed apparatus and method, routine 100 looks for a change of flow rate as measured, for example, by flow sensor 62. This change of flow rate is the difference between two different flow readings taken at two different pressure points at 108 (FIG. 3). For example, on curve 1 of FIG. 1, which is for a conventional patient interface device with variable exhaust flow from a fixed opening, at 7.5 cmH$_2$O the flow is about 22 SLPM, and at 15 cmH$_2$O the flow is about 32 SLPM. Hence, there is a flow change of 10 SLPM or about a 45.5% difference.

In contrast, for curve 5, which is for a patient interface device with PEV™ technology, at 7.5 cmH$_2$O the flow is about 18.5 SLPM, and at 15 cmH$_2$O the flow is about 19.5 SLPM. Here, there is a flow change of 1 SLPM or about a 5.4% difference over a 7.5 cmH$_2$O pressure gradient (i.e., 15 cmH$_2$O-7.5 cmH$_2$O for this example).

As a further example, a detecting range of the operating pressure of pressure support system 50 is preferably employed. For example and without limitation, if the detecting range is 25% of the operating pressure, then the pressure gradient is 7.5 cmH$_2$O (i.e., P2-P1) for an operating pressure up to 30 cmH$_2$O (i.e., 25% of 30 cmH$_2$O is 7.5 cmH$_2$O in this example). As another example, for a typical CPAP machine, if the normal range of operating pressure is 20 cmH$_2$O, then the 25% pressure gradient is 5 cmH$_2$O.

Although various example exhaust flow changes are disclosed, the routine 100 can operate, for example and without limitation, with such changes from 0% to about 25% or larger. One example range of the nil or minimal change in exhaust flow or intentional leak is from about 1% to about 5.4% depending on the pressure gradient (for example, for a relatively larger gradient there is a relatively higher percentage change, and for a relatively smaller gradient there is a relatively smaller percentage change). Although an ideal range of exhaust flow change of 0% could be achieved with relatively tighter tolerances, it might be impractical to achieve.

Although various pressure gradients are disclosed, the routine 100 can operate with non-limiting example pressure gradients of about 5% of the maximum pressure of pressure support system 50 (e.g., 1 cmH$_2$O for a common CPAP machine with a 20 cmH$_2$O pressure output range), about 25% of the maximum pressure of pressure support system 50, or about 50% of the maximum pressure of pressure support system 50 (e.g., greater than 10 cmH$_2$O for a common CPAP machine with a 20 cmH$_2$O pressure output range). For example and without limitation, the exhaust flow change can be proportional to the pressure range and depend upon the actual performance of the patient interface device.

Other non-limiting examples include flow changes of 5%, 10% and 25% for predetermined pressure gradients of 5%, 50% and 100%, respectively.

At 114 and during normal operation, routine 100 of FIG. 3 need not make variable compensation at different pressures due to changes in the purging flow rate. After routine 100 detects, for example and without limitation, a nil or minimal change in exhaust flow across a predetermined pressure gradient, it can make a suitable minimal adjustment to compensate for a fixed or approximately fixed flow rate across the entire operating pressure range.

EXAMPLE 6

Referring again to FIG. 1, an ideal "constant" flow curve, or plateau curve, like curve 2 provides a constant leak rate across a relatively wide range of pressure, which is above a predetermined pressure (e.g., without limitation, about 1.2 $cmH_2O$). Other curves, like curves 3-7, can make the flow respond more proportionally with the pressure at a relatively lower pressure range in order to reserve moisture, while allowing a near constant flow kick in at a designated pressure, such as for example, about 5 $cmH_2O$ in most of these curves. Hence, curves 3-7 provide a first flow that is proportional with pressure below a predetermined pressure and a second flow that is about constant above the predetermined pressure. This delay in the constant flow portion is designed mainly for CPAP or BiPAP users to treat sleep apnea. For COPD patients, effective $CO_2$ removal is vital to the therapy such that a relatively plateau effect is desired.

EXAMPLE 7

The disclosed apparatus and method preferably employ PEV™ (Plateau Exhalation Valve) technology and look for a nil or minimal change in exhaust flow across a significant pressure gradient to determine the specific patient interface device 58 (e.g., mask) in use. Such patient interface device 58 can include an external or built-in exhalation device employing PEV™ technology.

EXAMPLE 8

Although patient interface devices, such as 58, employing PEV™ technology are disclosed, the disclosed apparatus and method can function with conventional technology that does not employ PEV™ technology, although it may not apply to a conventional mask with a fixed opening exhaust. There, for example, for a fixed orifice, the flow change will exceed 50%.

EXAMPLE 9

Example applications for the disclosed apparatus and method include patient interface devices; and pressure support ventilating therapy or noninvasive positive airway pressure therapy, such as CPAP and Bi-Level, which employs an exhaust valve to purge $CO_2$.

The disclosed method and apparatus allow a potentially infinite expansion of the type of patient interface device 58 in use to be detected with a significant difference in exhaust flow characteristics in response to therapy needs without updating routine 100 (FIG. 3), since it looks, for example and without limitation, for a nil or minimal change in exhaust flow rate. Hence, steps 106, 108, 110, 112 can readily distinguish between curve 1 and curves 2-7 of FIG. 1. Hence, the mask type for curve 1 is manually entered at 116, while the mask types for curves 2-7 are advantageously automatically determined at 112. If a new patient interface device 58 is added, which meets the test at 110, routine 100 can either match the new device to one of the existing curves 2-7, or can add another curve to lookup table 118 by inputting, for example, its pressure-flow characteristic at a corresponding pressure point to lookup table 118. This is in complete contrast to known ventilators that solely rely on stored data in a fixed, predetermined database to look for a match. That approach has the disadvantage of limiting the number of patient interface devices to detect without upgrading such fixed, predetermined database.

Although the invention has been described in detail for the purpose of illustration based on what is currently considered to be the most practical and example embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support system comprising:
    a pressure generator;
    a pressure sensor;
    a flow sensor; and
    a controller cooperating with the pressure sensor and the flow sensor to control operation of the pressure generator, wherein the controller includes a processor and a stored routine executed by the processor, wherein the routine is structured to automatically identify a patient interface device in use with the pressure support system by:
    providing a plurality of pressures to the patient interface device using the pressure support system and determining a plurality of exhaust flow rates of the patient interface device, each exhaust flow rate being responsive to one of the plurality of pressures;
    detecting one or more nil or minimal changes of the exhaust flow rates responsive to provided pressures level changes when the plurality of pressures are above a certain predetermined onset pressure, wherein the nil or minimal change of the exhaust flow rate comprises a change in flow rate that is less than or equal to a predetermined flow variation tolerance; and
    comparing a particular one of the exhaust flow rates and a pressure corresponding to the particular one of the exhaust flow rates to a plurality of predetermined flow rates and a number of predetermined pressure points to identify the patient interface device, the particular one of the exhaust flow rates being responsive to one of the plurality of pressures that is above the certain predetermined onset pressure, wherein each of the provided pressures level changes each is at least 25% of a normal operating range of the pressure support system.

2. The pressure support system of claim 1, wherein the predetermined flow variation tolerance represents a change of 5.4% or less.

3. The pressure support system of claim 2, wherein the predetermined flow variation tolerance represents a change of 1% or less.

4. The pressure support system of claim 1, wherein each of the provided pressures level changes each is at least 5% of a maximum pressure of the pressure support system.

5. The pressure support system of claim 1, wherein the controller is further structured to automatically identify a type of mask as the automatically identified the patient interface device in use; and wherein the controller is further structured to control the pressure generator to provide pressure and flow to the mask based upon the type of mask.

6. The pressure support system of claim 1, wherein the controller is further structured to automatically identify the patient interface device in use at startup.

7. A method of automatically identifying a patient interface device in use with a pressure support system, the method comprising:
   providing a plurality of pressures to the patient interface device using the pressure support system and determining a plurality of exhaust flow rates of the patient interface device, each exhaust flow rate being responsive to one of the plurality of pressures;
   detecting one or more nil or minimal changes of the exhaust flow rates responsive to provided pressures level changes when the plurality of pressures are above a certain predetermined onset pressure, wherein the nil or minimal change of the exhaust flow rate comprises a change in flow rate that is less than or equal to a predetermined flow variation tolerance; and
   comparing a particular one of the exhaust flow rates and a pressure corresponding to the particular one of the exhaust flow rates to a plurality of predetermined flow rates and a number of predetermined pressure points to identify the patient interface device, the particular one of the exhaust flow rates being responsive to one of the plurality of pressures that is above the certain predetermined onset pressure.

8. The method of claim 7, further comprising employing the pressure support system for a pressure support ventilating therapy.

9. The method of claim 7, further comprising employing the pressure support system for one of pressure support ventilating therapy and noninvasive positive airway pressure therapy.

10. The method of claim 9, further comprising employing as the noninvasive positive airway pressure one of CPAP and Bi-Level pressure support therapy.

11. The method of claim 7, further comprising employing the pressure support system for one of COPD and sleep apnea therapy.

12. The method of claim 7, wherein each of the provided pressures level changes each is at least 25% of a normal operating range of the pressure support system.

13. The method of claim 7, wherein the predetermined flow variation tolerance represents a change of 5.4% or less.

14. The method of claim 7, further comprising controlling a pressure generator to provide pressure and flow to the mask based upon the type of mask.

15. The method of claim 13, wherein the predetermined flow variation tolerance represents a change of 1% or less.

16. The method of claim 7, wherein each of the provided pressures level changes each is at least 5% of a maximum pressure of the pressure support system.

* * * * *